(12) United States Patent
Wang et al.

(10) Patent No.: US 8,035,336 B2
(45) Date of Patent: Oct. 11, 2011

(54) CHARGER SLIPCOVER AND HANDHELD DEVICE

(75) Inventors: Ya-Ping Wang, Shanghai (CN); Yi-Feng Sun, Shanghai (CN); Shih-Kuang Tsai, Shanghai (CN)

(73) Assignee: Inventec Appliances Corp., Taipei Hsien (TW)

( * ) Notice: Subject to any disclaimer, the term of this patent is extended or adjusted under 35 U.S.C. 154(b) by 501 days.

(21) Appl. No.: 12/346,029

(22) Filed: Dec. 30, 2008

(65) Prior Publication Data

US 2010/0117589 A1  May 13, 2010

(30) Foreign Application Priority Data

Nov. 11, 2008  (TW) ................................ 97220218 U

(51) Int. Cl.
*H01M 10/44* (2006.01)
*H02J 7/00* (2006.01)
(52) U.S. Cl. ........................................ 320/101; 320/114

(58) Field of Classification Search .................. 320/101, 320/114
See application file for complete search history.

(56) References Cited

U.S. PATENT DOCUMENTS

| 6,977,479 B2 * | 12/2005 | Hsu ............................... 320/101 |
| 2008/0157712 A1 * | 7/2008 | Garcia ........................... 320/101 |
| 2008/0315828 A1 * | 12/2008 | Lu et al. ........................ 320/101 |
| 2009/0021214 A1 * | 1/2009 | Foster et al. .................... 320/114 |

* cited by examiner

*Primary Examiner* — M'Baye Diao
(74) *Attorney, Agent, or Firm* — Thomas, Kayden, Horstemeyer & Risley, LLP

(57) ABSTRACT

A charger slipcover and a handheld device comprising the charger slipcover are disclosed. The charger slipcover is suitable for charging a handheld device. The charger slipcover comprises a cover including a first portion and a second portion, wherein a handheld device body of the handheld device is suitable to being disposed on an inner surface of the second portion; a solar cell panel disposed on an inner surface of the first portion of the cover; and two conductive wires electrically connected to the solar cell panel and the handheld device body.

18 Claims, 4 Drawing Sheets

CHARGER SLIPCOVER AND HANDHELD DEVICE

RELATED APPLICATIONS

This application claims priority to Taiwan Application Serial Number 97220218, filed Nov. 11, 2008, which is herein incorporated by reference.

FIELD OF THE INVENTION

The present invention relates to a charger device and an application thereof, and more particularly to a charger slipcover and a handheld device comprising the charger slipcover.

BACKGROUND OF THE INVENTION

Current handheld devices, such as mobile phones, a personal digital assistants (PDAs) and electronic books are usually charged by chargers.

Refer to FIG. 1. FIG. 1 is a three-dimensional diagram of a conventional electronic book. A side of a conventional electronic book 100 is equipped with a DC jack 102, wherein the jack 102 is electrically connected to an internal control device, such as a motherboard of the electronic book 100. Typically, the conventional electronic book 100 is charged by an additional charger 104. When the electronic book 100 is charged, a plug 106 on one end of the charger 104 may be first inserted in the jack 102 of the electronic book 100, and a plug 108 on the other end of the charger 104 may be then inserted in a jack of a power supply, so that the electronic book 100 can be charged by the power supply.

The handheld device can be charged through a charger by adding a charge jack when designing the device, so that this conventional charge design is very simple and convenient and is widely used in the handheld device.

However, as a great deal of the global energy is consumed, the development and the application of green energy have become a tendency. The development and the use of solar energy have lasted a span, and this novel energy is not only environmental-protecting but also used circularly, so that the solar energy is desired to provide energy for a great majority of electronic products.

Refer to FIG. 2. FIG. 2 is a three-dimensional diagram of another conventional electronic book. An electronic book 200 mainly comprises a display module 204, an input module 206 and a solar energy module 208, wherein the display module 204, the input module 206 and the solar energy module 208 are all disposed in the interior of the electronic book 200. In addition, the display module 204, the input module 206 and the solar energy module 208 respectively form a display region 210, an input region 212 and a solar energy photo-sensing region 214. The electronic book 200 stores energy by using a photo-sensing device of the solar energy module 208 to absorb natural light, so as to provide the electronic book 200 in operation with the desired energy.

The solar energy module 208 is disposed in the electronic book 200, so that the size of the photo-sensing device in the solar energy module 208 is limited due to the limitation of the size of the electronic book 200. Such as shown in FIG. 2, the photo-sensing region 214 is much smaller than the display region 210, and thereby resulting in slow charging and small storage of the solar energy module 208. Therefore, the objective of completely using solar energy to fulfill the required energy of the product cannot be achieved by the current solar energy charge design.

Therefore, the majority of the current handheld devices still need to be equipped with charge jacks and are charged through the chargers, thereby cannot effectively conform to the tendency of green energy.

SUMMARY OF THE INVENTION

Therefore, one aspect of the present invention is to provide a charger slipcover suitable for a handheld device, which can provide a handheld device body with the desired energy by using solar energy conveniently and reliably.

Another aspect of the present invention is to provide a charger slipcover suitable for a handheld device, which can fully utilize solar energy to fulfill the energy requirement of the handheld device without increasing the number of components of the handheld device and the size of a body of the handheld device.

Still another aspect of the present invention is to provide a handheld device, which can effectively utilize solar energy as power energy, so that the handheld device has a benefit of energy saving and environmental protection, the convenience of use can be greatly increased, and the use cost can be reduced.

According to the aforementioned aspects, the present invention provides a charger slipcover suitable for charging a handheld device, wherein the charger slipcover comprises: a cover including a first portion and a second portion, wherein a handheld device body of the handheld device is suitable to being disposed on an inner surface of the second portion; a solar cell panel disposed on an inner surface of the first portion of the cover; and two conductive wires electrically connected to the solar cell panel and the handheld device body.

According to a preferred embodiment of the present invention, the cover may be a leather covering.

According to another preferred embodiment of the present invention, after the cover is folded up, the first portion and the second portion are piled up.

According to the aforementioned aspects, the present invention provides a handheld device comprising a handheld device body and a charger slipcover, wherein the charger slipcover is suitable for charging the handheld device body. The charger slipcover comprises: a cover including a first portion and a second portion, wherein the handheld device body is suitable to being disposed on an inner surface of the second portion; a solar cell panel disposed on an inner surface of the first portion of the cover; and two conductive wires electrically connected to the solar cell panel and the handheld device body.

According to a preferred embodiment of the present invention, the charger slipcover further comprises two sockets oppositely disposed on the inner surface of the second portion of the cover; and two conductive pillars respectively disposed on the sockets and electrically connected to two electrodes of the solar cell panel through the conductive wires respectively. In addition, the handheld device body comprises two holes, and the conductive pillars are respectively inserted in the holes to electrically connect the electrodes of the solar cell panel and the handheld device body.

DETAILED DESCRIPTION OF THE PREFERRED EMBODIMENT

The present invention discloses a charger slipcover and a handheld device including the same, wherein the charger slipcover is put around the handheld device and can provide the handheld device with the desired energy by using solar energy, thereby greatly increasing the convenience of charging the handheld device. In order to make the illustration of the present invention more explicit, the following description is stated with reference to FIG. 3 and FIG. 4.

Figure 1:
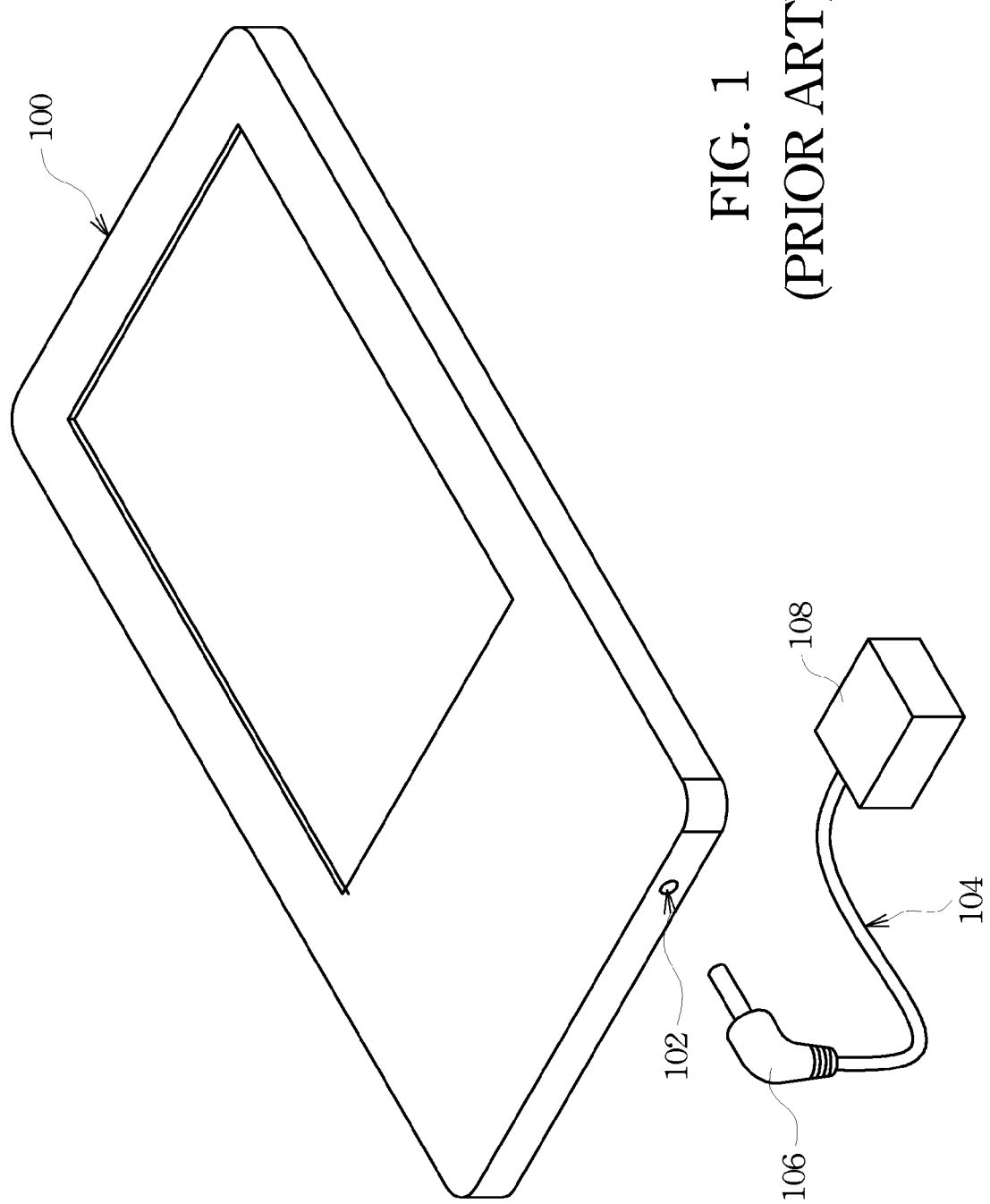
FIG. 1 is a three-dimensional diagram of a conventional electronic book.
Figure 2:
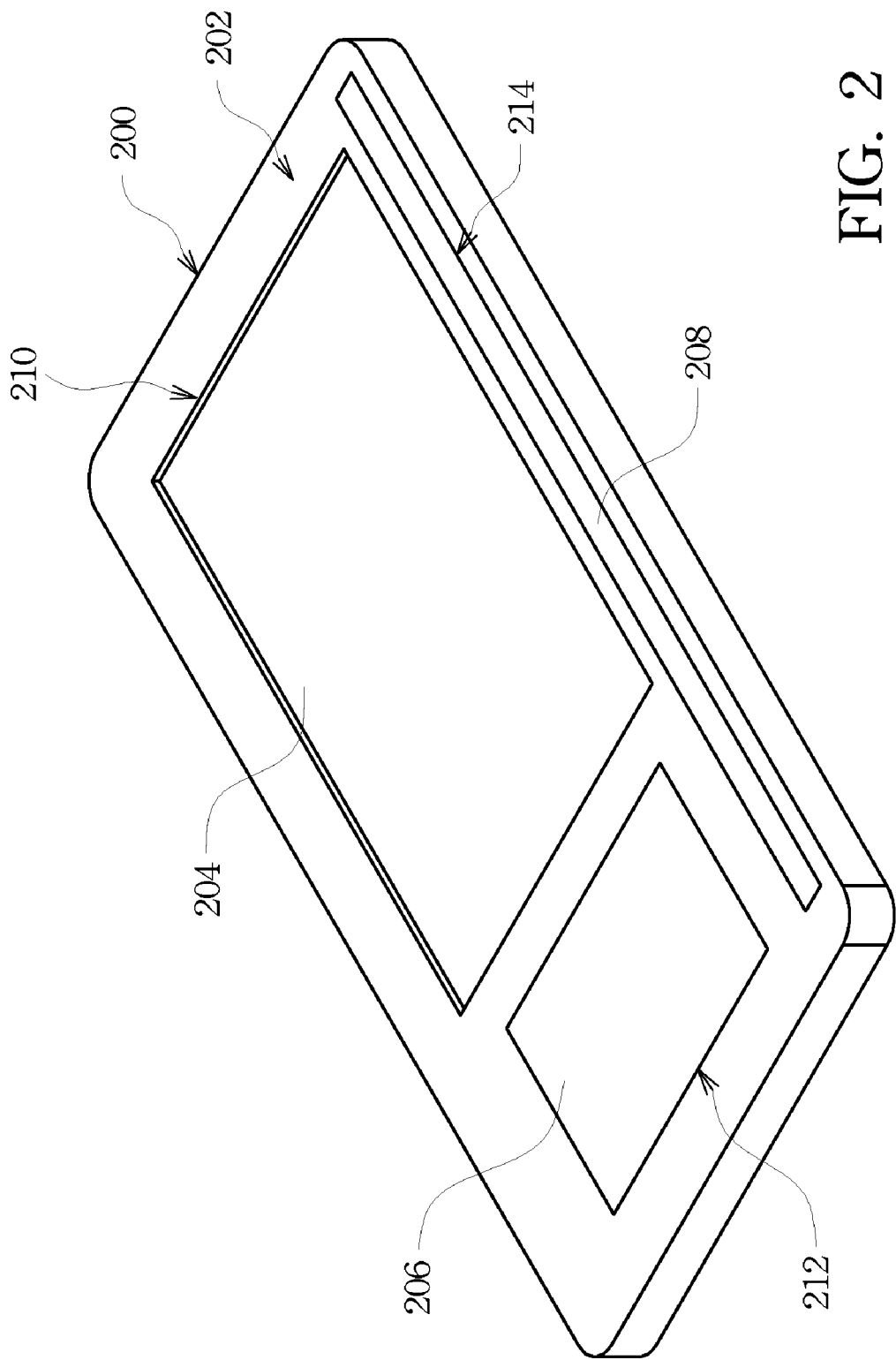
FIG. 2 is a three-dimensional diagram of another conventional electronic book.
Figure 3:
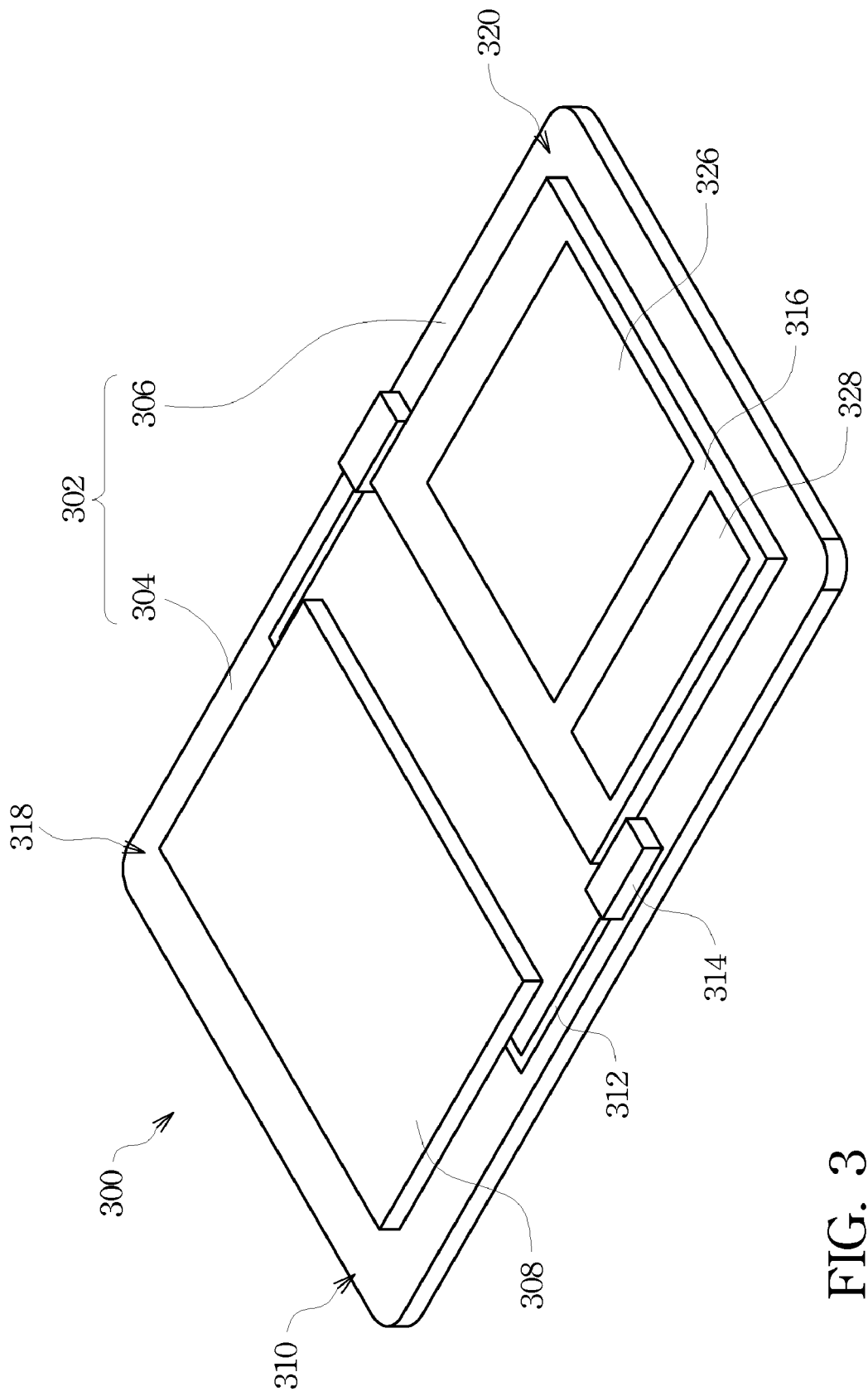
FIG. 3 is a three-dimensional diagram of a handheld device in accordance with a preferred embodiment of the present invention.
Figure 4:
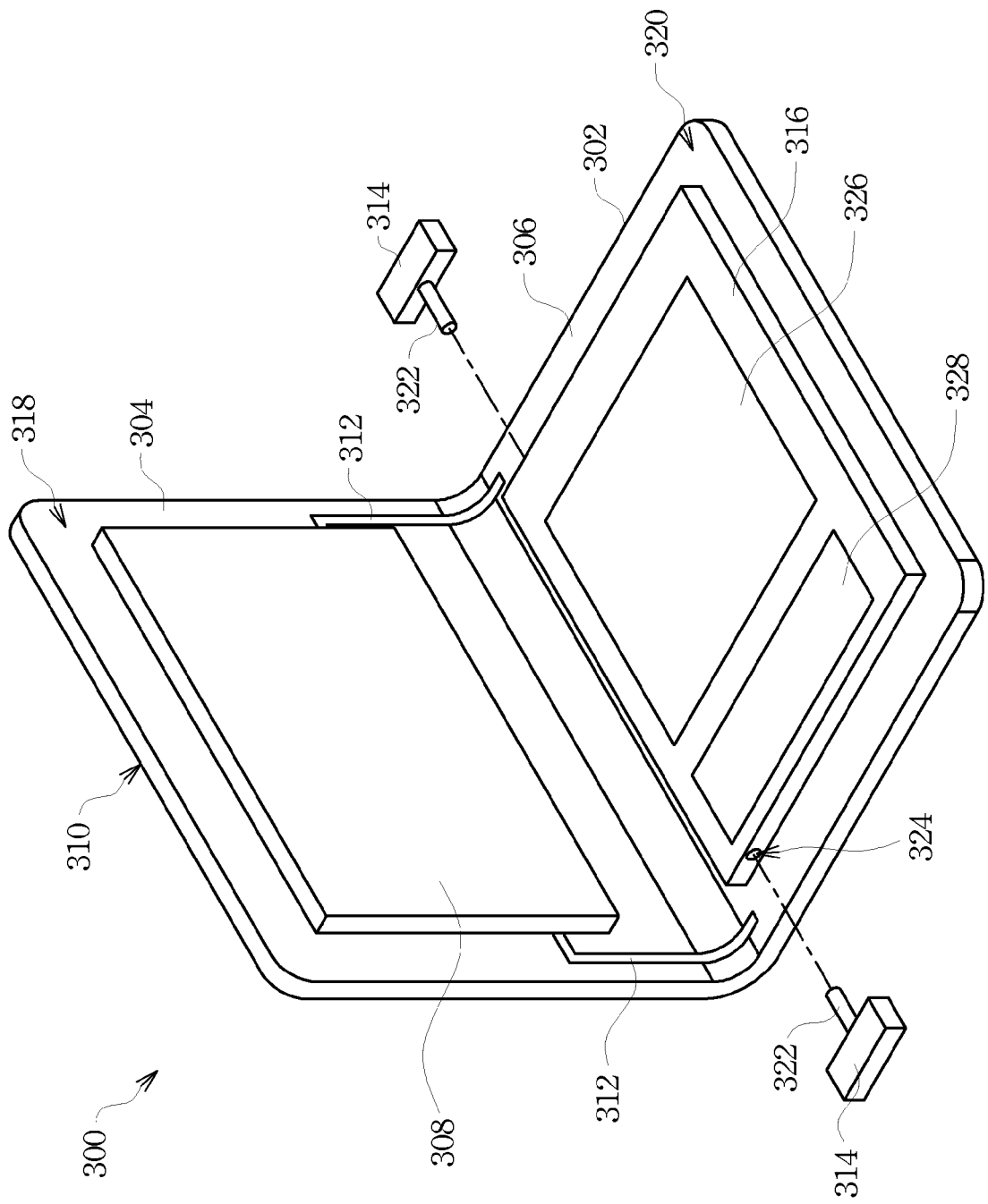
FIG. 4 illustrates an assembly diagram of a handheld device in accordance with a preferred embodiment of the present invention.

Refer to FIG. 3 and FIG. 4. FIG. 3 is a three-dimensional diagram of a handheld device in accordance with a preferred embodiment of the present invention, and FIG. 4 illustrates an assembly diagram of a handheld device in accordance with a preferred embodiment of the present invention. A handheld device 300 may be a low power-consuming handheld electronic product, such as an electronic book. In an exemplary embodiment, the handheld device 300 mainly comprises a handheld device body 316 and a charger slipcover 310, wherein the handheld device body 316 is disposed on the charger slipcover 310, the handheld device body 316 can be charged by conveniently and effectively using solar energy through the charger slipcover 310. The charger slipcover 310 comprises a cover 302, a solar cell panel 308 and two conductive wires 312, wherein the cover 302 may be a leather covering. Such as shown in FIG. 3, the cover 302 comprises a first portion 304 and a second portion 306, and the first portion 304 and the second portion 306 respectively includes an inner surface 318 and an inner surface 320, wherein the handheld device body 316 may be disposed on the inner surface 320 of the second portion 306 of the cover 302. In one embodiment, the cover 302 may be folded, and after the cover 302 is folded, the first portion 304 and the second portion 306 are piled up, and the inner surface 318 of the first portion 304 is opposite to the inner surface 320 of the second portion 306.

Such as shown in FIG. 3, the solar cell panel 308 is disposed on the inner surface 318 of the first portion 304 of the cover 302. The two conductive wires 312 can electrically connect the solar cell panel 308 and the handheld device body 316, wherein two electrodes (not shown) in the solar cell panel 308 are electrically connected to one end of each of the two conductive wires 312 respectively, and two electrodes (not shown) of the handheld device body 316 are electrically connected to the other end of each of the two conductive wires 312 respectively. In some embodiments, the charger slipcover 310 may selectively comprise two sockets 314, wherein the sockets 314 are preferably disposed on the inner surface 320 of the second portion 306 of the cover 302 respectively, and the sockets 314 are preferably disposed on two opposite sides of the inner surface 320. The sockets 314 can clip and be fixed to the handheld device body 316 disposed on the inner surface 320 of the second portion 306 of the cover 302. In an exemplary embodiment, the sockets 314 are preferably adjacent to the first portion 304 of the cover 302.

Simultaneously refer to FIG. 3 and FIG. 4. In an exemplary embodiment, the charger slipcover 310 may selectively comprise two conductive pillars 322, wherein the conductive pillars 322 are preferably disposed on the sockets 314 respectively. The conductive pillars 322 are composed of a conductive material. The two conductive pillars 322 are electrically connected to the conductive wires 312 respectively, so that the two conductive pillars 322 can be electrically connected to the two electrodes of the solar cell panel 308 respectively through the two conductive wires 312. In a preferred embodiment, the conductive pillars 322 respectively disposed on the sockets 314 may be opposite to each other, such as shown in FIG. 4. In another embodiment, the conductive pillars 322 are not opposite to each other, and the locations of the conductive pillars 322 are determined according to the locations of the two electrodes of the handheld device body 316 or the locations of the conductive elements electrically connected to the electrodes.

According to the product design, the handheld device body 316 may comprise a display module 326 and an input module 328, wherein the display module 326 is preferably an e-ink display module of low power-consuming, and the input module 328 may be a keyboard or a handwriting input module. In some embodiment, the handheld device body 316 may not include the display module 326 and the input module 328 according to the kind of the product. In the handheld device 300, the handheld device body 316 is disposed on the inner surface 320 of the second portion 306 of the cover 302 of the charger slipcover 310. Such as shown in FIG. 4, in an exemplary embodiment, the handheld device body 316 may selectively comprise two holes 324, wherein the holes 324 may be disposed on sides of the handheld device body 316, and the two holes 324 are electrically connected to the two electrodes of the handheld device body 316. The sizes and the locations of the holes 324 correspond to those of the conductive pillars 211 of the charger slipcover 310, so that the conductive pillars 322 of the charger slipcover 310 can be respectively and correspondingly inserted into the holes 324 of the handheld device body 316. When the conductive pillars 322 are inserted into the holes 324, the conductive pillars 322 are electrically connected to the two electrodes of the handheld device body 316. Such as shown in FIG. 4, in a preferred embodiment, the two conductive pillars 322 of the charger slipcover 310 are opposite to each other, and the two holes 324 of the handheld device body 316 are respectively disposed on opposite sides of the handheld device body 316, so that when the handheld device body 316 is disposed on the inner surface 320 of the second portion 306 of the cover 302 of the charger slipcover 310, the conductive pillars 322 of the charger slipcover 310 can be respectively and correspondingly inserted into the holes 324 of the handheld device body 316. In other embodiments, the locations of the holes 324 of the handheld device body 316 are determined according to the locations of the conductive pillars 322, so that the holes 324 of the handheld device body 316 may be disposed on the same side or on two adjacent sides of the handheld device body 316.

When the handheld device body 316 is disposed on the second portion 306 of the cover 302 of the charger slipcover 310, the conductive pillars 322 are respectively inserted in the holes 324 of the handheld device body 316, and the conductive pillars 322 are electrically connected to the corresponding holes 324 respectively, so that the two electrodes of the solar cell panel 308 are electrically connected to the two electrodes of the handheld device body 316 respectively through the two holes 324, the two conductive pillars 322 and the two conductive wires 312.

When the charger slipcover 310 is opened, the solar cell panel 308 can absorb the ambient light energy to produce electrical energy, and the electrical energy is transmitted to the handheld device body 316 through the two electrodes of the solar cell panel 308, the two conductive wires 312 and the two conductive pillars 322 of the charger slipcover 310, and the two holes 324 and the two electrodes of the handheld device body 316, so that the objective of using solar energy to charge the handheld device body 316 is achieved. The solar cell panel 308 is separately disposed on the first portion 304 of the cover 302 of the charger slipcover 310 without being disposed in the handheld device body 316, so that the size of the solar cell panel 308 is not limited by the size of the handheld device body 316, thereby can provide the handheld device body 316 with sufficient electrical energy to achieve the objective of completely using solar energy to provide the handheld device 300 with the desired energy.

According to the aforementioned embodiments of the present invention, one advantage of the present invention is that a charger slipcover suitable for a handheld device can provide a handheld device body with the desired energy by using solar energy conveniently and reliably.

According to the aforementioned embodiments of the present invention, another advantage of the present invention is that a charger slipcover suitable for a handheld device can fully utilize solar energy to fulfill the energy requirement of the handheld device without increasing the number of components of the handheld device and the size of a body of the handheld device.

According to the aforementioned embodiments of the present invention, still another advantage of the present invention is that a handheld device can effectively utilize solar energy as power energy, so that the handheld device has a benefit of energy saving and environmental protection, the convenience of use can be greatly increased, and the use cost can be reduced.

As is understood by a person skilled in the art, the foregoing preferred embodiments of the present invention are illustrated of the present invention rather than limiting of the present invention. It is intended to cover various modifications and similar arrangements included within the spirit and scope of the appended claims, the scope of which should be accorded the broadest interpretation so as to encompass all such modifications and similar structure.

What is claimed is:

1. A charger slipcover suitable for charging a handheld device, the charger slipcover comprising:
   a cover comprising a first portion and a second portion, wherein a handheld device body of the handheld device is suitable to being disposed on an inner surface of the second portion;
   a solar cell panel disposed on an inner surface of the first portion of the cover; and
   two conductive wires electrically connected to the solar cell panel and the handheld device body.

2. The charger slipcover according to claim 1, wherein the cover comprises a leather covering.

3. The charger slipcover according to claim 1, further comprising two sockets oppositely disposed on the inner surface of the second portion of the cover.

4. The charger slipcover according to claim 3, wherein the sockets are adjacent to the first portion of the cover.

5. The charger slipcover according to claim 3, further comprising two conductive pillars respectively disposed on the sockets and electrically connected to two electrodes of the solar cell panel through the conductive wires respectively.

6. The charger slipcover according to claim 5, wherein the conductive pillars are opposite to each other, the handheld device body comprises two holes respectively disposed on two opposite sides of the handheld device body, and the conductive pillars are suitable to being respectively inserted into the holes to electrically connect the electrodes of the solar cell panel and electrodes of the handheld device body.

7. The charger slipcover according to claim 1, wherein after the cover is folded up, the first portion and the second portion are piled up.

8. A handheld device, comprising:
   a handheld device body; and
   a charger slipcover suitable for charging the handheld device body, wherein the charger slipcover comprises:
      a cover comprising a first portion and a second portion, wherein the handheld device body is suitable to being disposed on an inner surface of the second portion;
      a solar cell panel disposed on an inner surface of the first portion of the cover; and
      two conductive wires electrically connected to the solar cell panel and the handheld device body.

9. The handheld device according to claim 8, wherein the charger slipcover further comprises two sockets oppositely disposed on the inner surface of the second portion of the cover.

10. The handheld device according to claim 9, wherein the sockets are adjacent to the first portion of the cover.

11. The handheld device according to claim 9, wherein the charger slipcover further comprises two conductive pillars respectively disposed on the sockets and electrically connected to two electrodes of the solar cell panel through the conductive wires respectively.

12. The handheld device according to claim 11, wherein the handheld device body comprises two holes, and the conductive pillars are suitable to being respectively inserted into the holes to electrically connect the electrodes of the solar cell panel and electrodes of the handheld device body.

13. The handheld device according to claim 12, wherein the conductive pillars are opposite to each other, and the holes are respectively disposed on two opposite sides of the handheld device body.

14. The handheld device according to claim 8, wherein after the cover is folded up, the first portion and the second portion are piled up.

15. The handheld device according to claim 8, wherein the cover comprises a leather covering.

16. The handheld device according to claim 8, wherein the handheld device comprises an electronic book.

17. The handheld device according to claim 8, wherein the handheld device comprises a display module.

18. The handheld device according to claim 17, wherein the display module comprises an e-ink display module.

* * * * *